United States Patent [19]

Youdin et al.

[11] 4,407,393
[45] Oct. 4, 1983

[54] PROPORTIONAL BRAKE FOR POWERED WHEELCHAIRS

[76] Inventors: Myron Youdin, 200 E. 33rd St., New York, N.Y. 10016; Mario W. Clagnaz, Jr., 18 Helen Ct., Floral Park, N.Y. 11001; Henry Louie, 2669 E. 23rd St., Brooklyn, N.Y. 11235

[21] Appl. No.: 266,623

[22] Filed: May 22, 1981

[51] Int. Cl.³ .............................................. B60T 7/02
[52] U.S. Cl. .................................. 188/2 F; 180/167; 188/162
[58] Field of Search .................. 46/256; 180/167, 168; 188/2 F, 72.3, 72.7, 162, 171

[56] References Cited

U.S. PATENT DOCUMENTS 3,013,624  12/1961  Remer et al. ................... 188/162 X
4,207,959  6/1980   Youdin et al. ...................... 180/167

Primary Examiner—Duane A. Reger
Attorney, Agent, or Firm—Darby & Darby

[57] ABSTRACT

A braking system for a powered wheelchair is disclosed which provides means for the brakes to be activated by a quadraplegic operator. The system provides the operator with the ability to apply the brakes either fully or partially, or to apply the brakes intermittently without completely stopping the chair. When power to the system is turned off, the brakes remain in the state of activation which they were in prior to the interruption.

11 Claims, 6 Drawing Figures

PROPORTIONAL BRAKE FOR POWERED WHEELCHAIRS

This invention relates to motorized wheelchairs and, more particularly, toward a proportional braking system for such a wheelchair which is adapted to be activated by means such as voice command or breath control.

A need has been recognized for some time for a reliable braking system for powered wheelchairs suitable for use by persons with quadraplegia or other severe neuromuscular disorders. This need has become especially compelling because of a great increase in a number of spinal cord injuries in the United States in recent years. Such a braking system must be designed in a manner which allows it to be readily understood and easily operated by a patient with little or no technical ability or aptitude.

U.S. Pat. No. 4,207,959 of Youdin et al, describes a powered wheelchair which is particularly suited for use by quadraplegics by nature of its ability to be controlled either by voice commands or by puffing or sipping into appropriately positioned tubes. The wheelchair described in the '959 patent has individually controllable drive motors for its left and right drive wheels, respectively. It is capable of recognizing a number of spoken "function" commands which cause the left and right drive motors to be activated in a manner to produce the specified movement of the wheelchair. In a preferred embodiment, six "function" commands are utilized: FORWARD; REVERSE; LEFT; RIGHT; FASTER; and SLOWER. The FORWARD and REVERSE commands result in the wheelchair drive motors being conditioned to rotate in the same direction and at the same speed so as to propel the wheelchair in a straight path in the specified direction. The LEFT and RIGHT commands respectively condition an increase in speed at the appropriate drive motor thus causing the wheelchair to turn in the specified direction. The FASTER and SLOWER commands respectively condition equal acceleration or deceleration of both of the drive motors.

In the preferred embodiment of the apparatus described in the '959 patent, the utterance of one of the above "function" commands does not actually cause the specified function to be performed, but merely conditions the apparatus to perform the function upon the utterance of a subsequent "activation" command. These "activation" commands are a GO command which causes the unconditional execution of the previously specified function and a JOG command which causes the previously specified function to be executed for a limited period of time. Various means are described for varying the duration of the time period.

In addition to the above commands, the apparatus set forth in the '959 patent also recognizes a STOP command which causes execution of the previously specified wheelchair function to be immediately terminated (that is, both drive motors are turned off immediately). A BRAKE command is also provided which in addition to turning off the wheelchair motors also activates the wheelchair brakes.

The means provided for braking in the '959 patent is effective as an emergency braking system but is impractical for use in other situations because it only allows the brakes to be fully applied or not to be applied at all.

As a result of research involving disabled wheelchair users, it has been determined that an optimum braking system is one which operates in a manner analogous to the braking system of an automobile. This conclusion follows from the fact that most disabled patients were drivers prior to their disabling accident, and are thus thoroughly familiar with the operation of such a system. Such an optimum or "ideal" braking system is believed to have the following attributes:

1. The brakes may be applied as required by the wheelchair's operator in situations similar to those in which he would apply the brakes if he were driving an automobile;

2. The brakes may function as auxiliary parking/transfer brakes provided they can be released without the need for any separate manual disconnect;

3. The brakes should operate independently of the wheelchair drive motors;

4. The braking action should be proportional, that is, the system should be capable of allowing the operator to select the amount of braking force to be applied; and 5. The braking controls should not be interconnected to the speed controls.

It will be noted that of the above attributes, the only one which is possessed by the braking system set forth in the '959 patent is the ability of the brakes to be used as a parking/transfer brakes.

The braking system of the '959 patent is not capable of allowing the driver to apply the brakes as required in situations similar to those in which he would apply the brakes if he were driving an automobile. For example, in driving an automobile one may wish to apply the brakes intermittently while travelling downhill to prevent the vehicle from accelerating too rapidly. The braking system of the '959 patent does not allow the wheelchair operator to apply the brakes in such a manner because when a BRAKE command is issued the wheelchair drive motors are immediately turned off and the brakes are fully applied to completely stop the wheelchair.

The attribute of the "ideal" system requiring the brakes to operate independently of the wheelchair drive motors is not satisfied by the '959 system since its BRAKE command affects the operation of both the drive motors and the brakes.

The proportional braking attribute of the "ideal" system is also not satisfied by the '959 system where the brakes are limited to being either fully disengaged or fully engaged. Thus, an operator of a wheelchair in accordance with the '959 patent cannot control the amount of braking force applied, or the rate of deceleration of the wheelchair.

It is an object, therefore, of the present invention to provide a braking system for a powered wheelchair which allows the brakes to be applied as required by the operator in situations similar to those in which he would apply the brakes if he were driving an automobile.

It is a further object of the invention that the brakes of the wheelchair be adapted to function as auxiliary parking/transfer brakes.

It is a further object of the invention that the brakes operate independently of the wheelchair drive motors.

It is still another object of the invention to provide a braking control system for a powered wheelchair which allows the brakes to be applied intermittently to slow, but not stop, the chair, and which provides means for allowing the operator to select the amount of braking force to be applied.

It is a still further object of the invention to provide a brake control apparatus for a powered wheelchair which is not interconnected to the speed controls.

GENERAL DESCRIPTION

In accordance with an illustrative embodiment of the the invention, a braking control means is provided which includes, an electric brake activation motor which may be activated, under control of the operator, to rotate a shaft by a desired angular amount. The rotational movement of the shaft is converted to a corresponding braking force. This conversion may be accomplished, for example, by coupling the shaft of the motor to the master cylinder of a hydraulic braking system by suitable means such as a cam and a pivotally mounted member. The hydraulic system, in turn, constitutes the brake activation means for the system. The arrangement of the above elements is such that the amount of force applied by the brakes is related to the angular position of the cam.

In one embodiment of the invention, the amount of rotation of the brake activation motor is selected by apparatus which is responsive to spoken commands.

In another embodiment of the invention, rotation of the motor is responsive to the opening and closing of appropriate pressure switches which are responsive to the operator puffing or sipping into a small tube.

The foregoing brief description, as well as further objects, features and advantages of the present invention will be more fully understood by reference to the following detailed description of an illustrative embodiment of the invention when taken in conjunction with the accompanying drawings wherein.

DESCRIPTION OF THE PREFERRED EMBODIMENT

Figure 1:
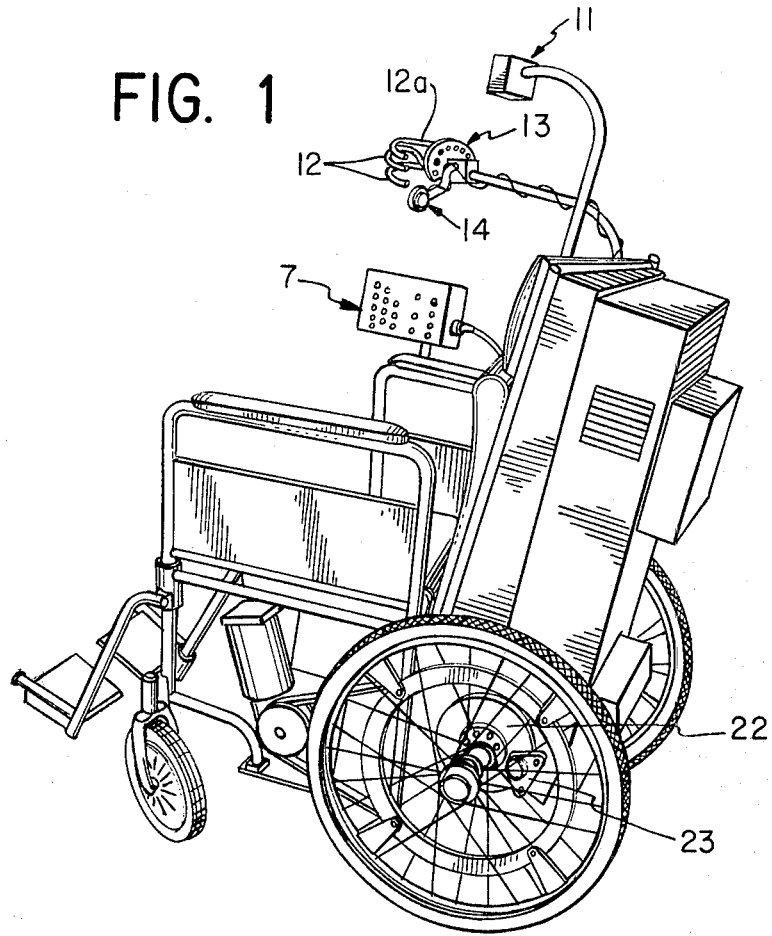
FIG. 1 is a pictorial representation of a powered wheelchair equipped with the braking apparatus of the present invention.

FIG. 1 shows a powered wheelchair equipped with the proportional braking system of the present invention. The wheelchair of FIG. 1 is similar to that described in U.S. Pat. No. 4,207,959 except for additions which provide the operator of the wheelchair with the ability to apply brakes in a proportional manner.

The elements of the wheelchair of FIG. 1 which were also present in the wheelchair of the '959 patent include a microphone 14 which is positioned sufficiently close to the operator's mouth so that extraneous noise does not interfere with the wheelchair commands spoken by the operator. A display panel 7 provides the operator with a visual indication of the status of operations being performed by the wheelchair apparatus. A speed indicator 13 gives a visual indication to the operator regarding the speed which the wheelchair has previously been conditioned to attain by a prior voice command. An emergency stop switch 11 is positioned sufficiently close to the operator's head so that a small movement of the head will cause the emergency switch to be activated. Activation of the emergency switch overrides the wheelchair's controls and turns off power to the drive motors.

The wheelchair of FIG. 1 is also provided with a pair of breath control tubes 12 which are adapted to be used in connection with a "puff-and-sip" wheelchair control system such as the one described in a paper of Youdin et al, Proceedings of the Fourth Annual Conference on Systems and Devices for the Disabled, June 1977, pp. 147–50. As described in greater detail in this article, such breath control tubes may be utilized to provide the operator of the chair with the ability to cause the chair to move forward or backward, to the left or to the right, and faster or slower. In the present apparatus, a third breath control tube 12a may be additionally provided in order to give the operator of the wheelchair the ability to control the wheelchair brake in a "puff-and-sip" manner.

It is within the scope of the present invention for control of the brakes to be obtained by either spoken command, or by the "puff-and-sip" method. In a preferred embodiment, however, the wheelchair is capable of being controlled either by voice command or by "puff-and-sip" and the control apparatus is adapted to override voice activated controls with controls activated by the breath control tubes. This dual method of activating the wheelchair control is desirable to prevent potentially dangerous situations from occurring if, for example, the voice operated controls malfunction.

Figure 2:
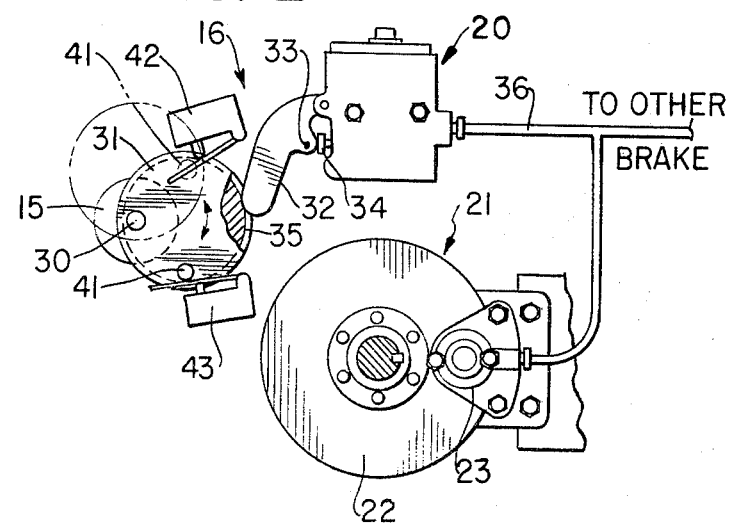
FIG. 2 is a pictorial representation of an embodiment of the braking apparatus of the present invention.

An embodiment of the proportional wheelchair braking control apparatus in accordance with the present invention is shown in FIG. 2. It has control means which in this embodiment is an electric brake activation motor 15 which is connected through a linkage 16 to brake activation means of the system. This brake activation means includes a hydraulic master brake cylinder 20. This master cylinder 20 is in turn connected through hydraulic lines 36 to a brake 21 at one or both of the drive wheels. In the presently preferred embodiment these brakes are disc brakes including a disc 22 and a caliper 23.

The electric brake activation motor 15 is, preferably, of the direct current type. The motor should be adapted to rotate in either a clockwise or a counterclockwise direction depending upon the direction of current flow through the motor. Application of current through the motor 15 for relatively short time duration should cause the motor to rotate by a correspondingly small angular increment.

The linkage 16 which connects the motor 15 to the master cylinder 20 provides means for converting the rotational motion of the motor to a "braking signal" which in the embodiment illustrated is a substantially linear motion of a piston rod 34 of the master cylinder 20. The linkage includes a shaft 30 which may be either the motor shaft or an extension of the motor shaft connected to it by suitable means. The shaft 30 is connected to a cam 31 which is positioned to make contact with a lever 32 which is pivotably mounted to the master cylinder. The lever 32 has a protrusion 33 which makes contact with the piston rod 34 of the master cylinder. The cam 31 preferably has a groove 35 formed about its circumference and dimensioned to accept the lever 32 which makes sliding contact with the cam 31. The shape and dimensions of the cam 31 and the point at which the shaft 30 is mounted to it are selected so that a given angular rotation of the shaft 30 by the motor 15 will produce a proportional linear displacement of the piston rod 34 by causing the protrustion 33 of the lever 32 to be urged toward or away from the piston rod 34.

The master cylinder 20 is connected by hydraulic lines 36 to the hydraulic calipers 23 of the brakes 21 of the wheelchair.

The operation of the braking apparatus of FIG. 2 is as follows. When the brakes are fully disengaged, the cam 31 is in the position indicated by the phantom lines of FIG. 2. With the cam 31 in this position, the lever 32 is at a position at which the piston rod 34 of the master cylinder is at the limit of its possible outward movement and no pressure is generated in the master cylinder 20.

When the motor 15 is activated to rotate the cam 31 in a clockwise direction, the cam 31 urges the bottom portion of the lever 32 in a left to right direction in the diagram. The movement of the lever 32 urges the piston rod 34 from left to right until it reaches a fully depressed position as shown by the solid lines in FIG. 2. With the piston rod 34 in such a fully depressed position, the fluid within the hydraulic master cylinder 20 is fully pressurized thus causing the hydraulic caliper 23 to engage the disc 21 with maximum braking force.

It will be noted that if the motor 15 causes the cam 31 to rotate to an intermediate position between the positions illustrated by the solid and phantom lines of FIG. 2, the piston rod 34 will be only partially depressed. In this situation, the pressure generated in the master cylinder 20 will be less than full braking pressure. Such a "partial" braking pressure causes the hydraulic caliper 23 to engage the disc 22 with less force than would be the case if full braking pressure had been applied. Such an application of partial braking pressure is useful, for example, where it is desired to slow but not stop the vehicle, or where it is desired to slow the vehicle to stop in a gradual manner.

It will be appreciated that it would be undesirable to allow the cam 31 to rotate freely through angles greater than the rotational angle necessary to produce a movement of the lever 32 which suffices to move the piston rod 34 through its maximum range of movement. Such free movement of the cam could, for example, cause the brakes to be intermittently applied and released. It is important therefore that the braking apparatus of FIG. 2 include means for limiting the movement of the cam 31 to be within a predetermined angular range.

An illustrative embodiment of this limiting means is shown in FIG. 2 as comprising a protrusion 41 on the cam 31, and a pair of limit switches 42 and 43. The positional relationship of the limit switch 42 and the protrusion 41 is selected so that when the cam 31 is rotated counterclockwise to a position at which the piston rod 34 is at its maximum range of movement out of the cylinder 20, protrusion 41 engages and depresses the arm of switch 42 as indicated by the phantom lines. The position of switch 43 is selected so that the arm of switch 43 is depressed by the protrusion 41 when cam 31 rotates clockwise to a position at which the piston rod 34 is fully depressed. As set forth below, in the discussion of FIG. 3, switches 42 and 43 may be used to disconnect power from the motor 15 when the piston rod 34 reaches its fully extended or fully depressed position.

Figure 3:
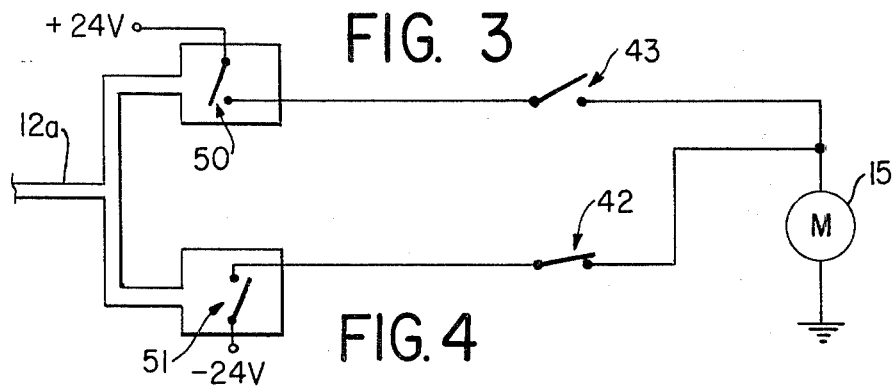
FIG. 3 is a circuit diagram of an interface which provides control of the braking apparatus of FIG. 2 by means of a puff and sip tube.

FIG. 3 shows an illustrative embodiment of circuitry adapted to allow the operator to select the amount of braking force to be applied to the wheelchair brake by the "puff-and-sip" method. In this embodiment, one terminal of the brake control motor 15 is connected to system ground (actual ground is not available because of the rubber tires of the wheelchair). The other terminal of the motor 15 is connected through the switch 43 to one terminal of a pressure switch 50. The second terminal of the motor 15 is also connected through the switch 42 to one terminal of a pressure switch 51. The other terminals of switches 50 and 51 are connected respectively to a +24 volt supply and a −24 volt supply.

Pressure switches 50 and 51 are switches which may be activated by the application to them of pressures greater than or less than atmospheric pressure. An example of such a switch which is particularly adapted for use in the present apparatus is a Fairchild Instrument Co. PSF 100A Pressure Sensor. The housings of switches 50 and 51 are connected to the breath control tube 12A. In the present embodiment, switches 50 and 51 are both selected to be normally open. Switch 50 is adapted to close when a pressure greater than atmospheric pressure is applied to it as when the operator of the wheelchair "puffs" into the breath control tube 12a. Switch 51 is adapted to close when a pressure less than atmospheric pressure is applied into it as when the wheelchair operator sips on breath control tube 12a. It will be noted that when pressures at or near atmospheric pressure are applied to switches 50 and 51 they both remain open. Thus, during the interval or transition between a "puff" and a "sip" both switches will open. This characteristic of the switches effectively prevents the possibility of switches 50 and 51 both being closed at the same time which would result in shortcircuiting the +24 volt and −24 volt power supplies.

Switches 42 and 43 are both normally closed switches which are urged to their open positions by protrusion 41 under the conditions discussed above. FIG. 3 illustrates the position of all the switches when the brakes are fully engaged and the cam 31 has been rotated to the limit of its permissible clockwise rotation, and the operator of the wheelchair is neither puffing nor sipping into the breath control tube 12a.

It will be noted that in this condition, if the wheelchair operator puffs into breath control tube 12a, a pressure greater than atmospheric pressure will be applied to the pressure switch 50 thus causing it to close. However, since the switch 43 remains open no voltage is applied to the motor 15 and thus no further rotation of the motor occurs.

When the operator wishes to release the brakes, he sips upon the breath control tube 12a thereby applying a pressure less than atmospheric pressure to the pressure switch 51 which in turn causes switch 51 to close. Since switch 42 is closed at this time, the closing of switch 51 allows −24 volts to be applied to the motor 15 thereby causing motor 15 to begin to rotate in a counterclockwise direction. As previously set forth, this counterclockwise rotation results in the hydraulic pressure to the wheelchair brakes being reduced. This reduction in hydraulic pressure continues as long as the operator continues to sip on breath control tube 12a or until the cam 31 of FIG. 2 reaches the limit of its counterclockwise rotation at which time the limit switch 42 is urged into an open position.

It will be appreciated that as soon as the cam 31 of FIG. 2 begins its counterclockwise rotation, the switch 43 is allowed to close. During any time period in which the switch 43 is closed puffing into breath control tube 12a closes switch 50 thereby connecting the +24 volt power supply to the motor 15 which causes clockwise rotation of the motor and a resulting increase in hydraulic pressure to the brakes.

It is a feature of the present system that when the wheelchair power is turned off, the cam 31 remains in the position it was at just prior to turning the power off. Thus, the brakes may be used as parking or transfer brakes by causing the brakes to be fully engaged before turning power off. The brakes will remain in their fully engaged position after power has been turned off.

Figure 6:
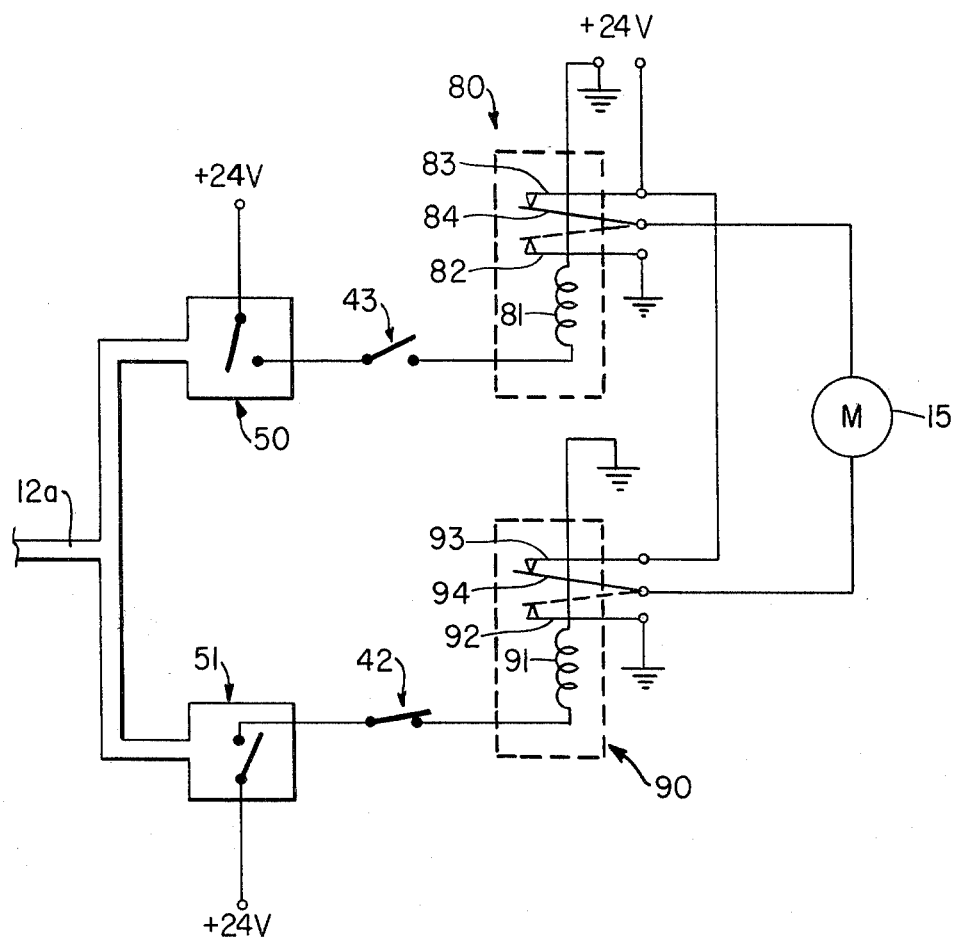
FIG. 6 is a circuit diagram of an interface utilizing relays to provide control of the braking apparatus of FIG. 2.

FIG. 6 shows another embodiment of an electrical interface which provides means for allowing the operator to select the amount of braking force to be applied by the "puff-and-sip" method. This embodiment is similar to the embodiment illustrated by FIG. 3 except for its use of relays to control the activation of the motor 15. An advantage of the embodiment of FIG. 6 is that it requires only a single +24 volt power supply.

Referring to FIG. 6, it will be noted that the pressure switches 50 and 51, the limit switches 42 and 43, and the motor 15 are identical to the corresponding elements illustrated in FIG. 3. In the embodiment of FIG. 6, however, pressure switch 51 is connected to a +24 volt power supply instead of the −24 volt power supply utilized in FIG. 3. A relay 80 having a coil 81, a normally open contact 82, a normally closed contact 83, and an armature 84, is connected between the limit switch 43 and the motor 15 as follows. The coil 81 is connected between the limit switch 43 and ground. The normally closed contact 83 is connected to the +24 volt supply and the normally open contact 82 is connected to ground. The armature 83 is connected to one side of the motor 15.

A relay 90 having a coil 91, a normally open contact 92, a normally closed contact 93, and an armature 94 is connected between the limit switch 42 and the other side of the motor 15 in a manner similar to the manner of connection of the relay 80.

FIG. 6 illustrates the condition or state of the circuitry which exists when the wheelchair brakes are fully engaged and when the operator is neither puffing nor sipping into the breath control tube 12a. In this condition, pressure switches 50 and 51 are both open and thus neither coil 81 nor coil 91 is connected to the +24 volt supply. With neither of these coils energized, armature 84 remains in contact with normally closed contact 83 of relay 80, and armature 94 remains in contact with the normally closed contact 93 of relay 90. With the armatures 84 and 94 in these positions, both sides of the motor 15 are connected to the +24 volt supply, and, thus, no current flows through the motor 15.

When the operator wishes to release the brakes, he sips into the breath control tube 12a, thus causing pressure switch 51 to close. The closing of pressure switch 51 energizes relay coil 91 by connecting it to the +24 volt power supply. The energizing of coil 91 causes armature 94 to engage the normally open contact 92 of relay 90 as indicated by the broken line in the diagram. With armature 94 in this position, the bottom side of the motor 15 is connected to ground through the armature 94 and the contact 92. The top side of the motor 15 remains connected to the +24 volt power supply through armature 84 and relay contact 83, and current thus flows from top to bottom through the motor 15 causing a counterclockwise rotation of the motor. This counterclockwise rotation causes the brakes to be released as described above.

As set forth previously, limit switch 43 is allowed to close as soon as the motor 15 begins its counterclockwise movement. If the operator of the chair puffs into the breath control tube 12a to cause additional braking force to be applied, pressure switch 50 closes. The closing of pressure switch 50 completes a circuit from the +24 volt power supply through pressure switch 50, limit switch 43, and coil 81, to ground thus energizing the coil 81. The energizing of coil 81 causes the armature 84 to engage the normally open contact 82 of relay 80. In this condition of the circuitry, ground is connected to the top side of the motor 15 through relay contact 82 and the armature 84. The bottom of the motor 15 is connected to the +24 volt supply through the armature 94 and relay contact 93 since coil 91 must be deenergized at this time (puffing into breath control tube 12a causes pressure switch 51 to open thus deenergizing coil 91). Current now flows from the +24 volt supply through relay contact 93 and armature 94 in a bottom-to-top direction through motor 15 and thence to ground through armature 84 and relay contact 83. This flow of current causes a clockwise rotation of the motor 15 which results in the application of additional braking force as described previously.

Figure 4:
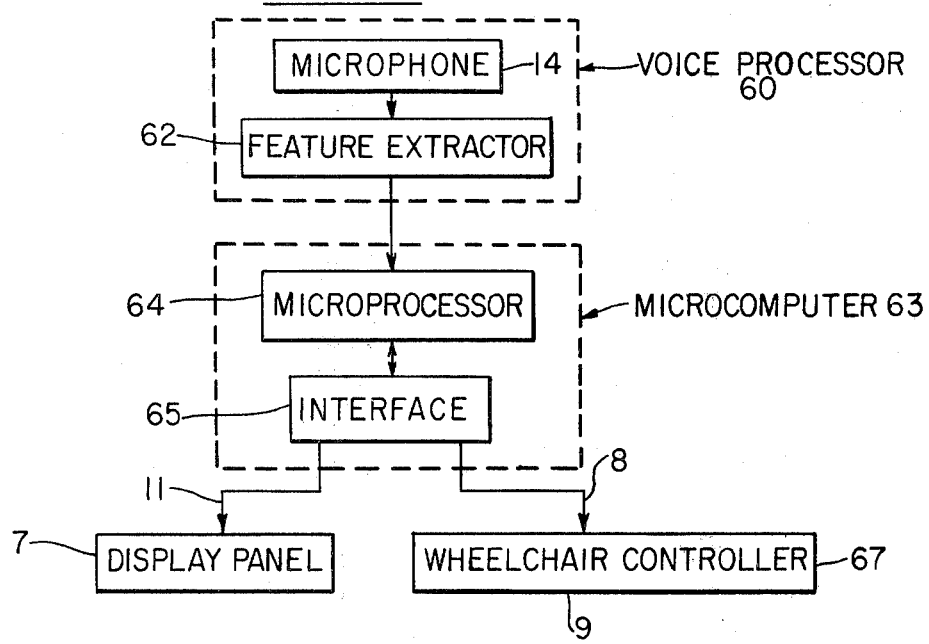
FIG. 4 is an overall block diagram of a prior art apparatus for providing control of a powered wheelchair by spoken commands.

The braking apparatus of the present invention is also suitable to be used in conjunction with a voice controlled wheelchair such as that described in U.S. Pat. No. 4,207,959. FIG. 4 is a simplified block diagram of the control apparatus of his wheelchair. The major components of this control apparatus are a voice processor 60, a microcomputer 63, the display panel 7 and a wheelchair controller 67. The braking apparatus of FIG. 2 may be considered to be included in the wheelchair controller 67.

Voice processor 60 includes: the microphone 14 which picks up the spoken commands and converts them into electrical signals; and a feature extractor 62 which converts these electrical signals into a form which is suitable for processing by the microcomputer 63.

Microcomputer 63 includes a microprocessor 64 which is programmed to recognize signals from the feature extractor 62 which represent valid spoken commands for the wheelchair. In response to these signals, the microprocessor 64 activates corresponding individual signal paths in the interface 65. These individual signal paths are connected to the wheelchair controller 67 where they activate appropriate circuitry for causing the wheelchair to carry out the action specified by the spoken commands.

Figure 5:
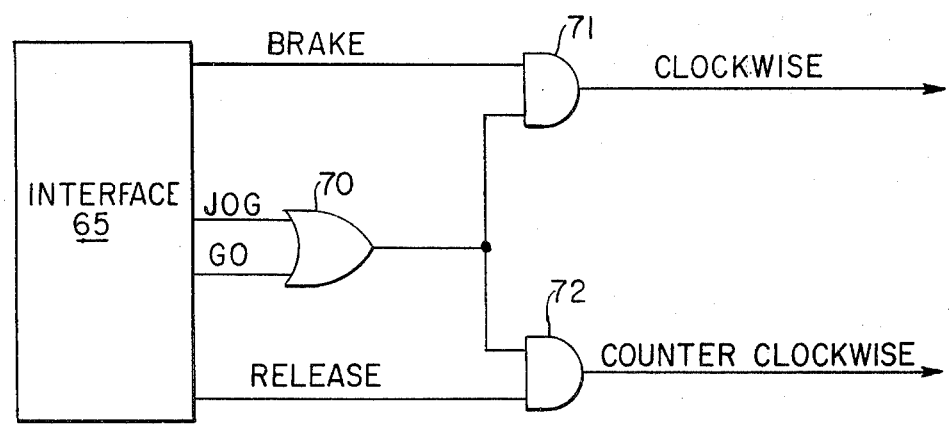
FIG. 5 is a logic diagram of an interface which provides control of the braking apparatus of FIG. 2 by means of the voice control apparatus of FIG. 4.

FIG. 5 is an illustration of interface logic circuitry which may be used in conjunction with appropriate signal paths from the interface 65 to allow the wheelchair operator to select the amount of braking force to be applied by the spoken command.

As illustrated by FIG. 5, interface 65 produces a BRAKE signal and a RELEASE signal. These signals are activated as a result of corresponding spoken BRAKE or RELEASE commands which are considered to be "function" commands as described previously. Interface 65 also may provide a JOG or a GO signal as a result of corresponding spoken "activation" commands. Typically, the GO signal is active from the time the GO command is uttered to some subsequent time at which another command is uttered which causes the deactivation of the GO signal. The JOG signal, on the other hand, is active only for a limited duration of time subsequent to the utterance of the JOG command. The duration during which the JOG signal is active may be controlled by various means as set forth in much more detail in the '959 patent.

The JOG signal and the GO signal are fed into an OR gate 70, the output of which is connected to respective input terminals of an AND gate 71 and an AND gate 72. A second input terminal of the AND gate 71 is connected to the BRAKE signal path and a second input terminal of the AND gate 72 is connected to the RELEASE signal path. The output of the AND gate 71 is a signal which may be utilized to condition clockwise rotation of the brake control motor 15 of FIGS. 2 and 3 thus applying the wheelchair brakes as previously discussed. The output of the AND gate 72 is a signal which conditions counterclockwise rotation of the brake control motor 15 thereby releasing the brakes. The conditioning function of these "clockwise" and "counterclockwise" signls may be implemented, for example, by replacing pressure switches 50 and 51 of FIG. 2 with relays which are controlled by the above signals.

The operation of the circuitry illustrated by FIG. 5 is as follows. Upon the utterance of a BRAKE command the BRAKE signal is activated thereby conditioning one leg of the AND circuit 71. If the next spoken command is the activation command GO, the GO signal is activated thereby causing the activation of a signal at the output of the OR gate 70 which consequently activates the second input leg of the AND gate 71. Under these conditions the AND gate 71 produces a "clockwise" motor rotation signal. This signal causes the brake control motor 15 to rotate in a clockwise direction until its motion is stopped by the activation of the limit switch 43 as previously discussed.

If, on the other hand, the first spoken command after the BRAKE command is the function command JOG, the JOG signal becomes activated for a limited duration of time. The second input leg of the AND circuit 71 is thus activated for a corresponding time duration. Under these conditions the output of the AND circuit 71 is activated for a duration which results in a clockwise rotation of the motor 15 sufficient only to cause partial braking pressure to be generated. The wheelchair consequently decelerates in a gradual manner. If it is desired to increase the braking pressure, the JOG command may be repeated. Each repetition of the JOG command causes additional rotation of the brake activation motor 15 until the limit of its rotation is reached.

Similarly, release of the brakes may be accomplished in an immediate manner by uttering a RELEASE command followed by a GO command or in a gradual manner by uttering a RELEASE command followed by one or more JOG commands.

It will be appreciated that the above description is for purposes of illustration only and that many modifications are possible without departing from the spirit or scope of the invention. For example, in the embodiment of the invention wherein the brakes are activated by voice command it is not strictly necessary to utilize the JOG command or GO command for applying the brakes. Alternatively, the microcomputer may be programmed to cause a limited duration activation of the BRAKE signal upon the utterance of a BRAKE command. Subsequent BRAKE commands would, in this case, cause additional activations of the BRAKE signal. Each utterance of the BRAKE command in this case would cause additional partial braking pressure to be generated in the hydraulic system.

Another example of a possible modification is one in which the embodiment of the invention illustrated by FIG. 3 is modified to allow control of the brakes by means other than a breath control tube. In such a modification, pressure switches 50 and 51 may be replaced by switches suitable for being operated by, for example, movements of the operator's head, or movement of a "joystick" or other type of lever.

What is claimed is:

1. A proportional braking system for a powered wheelchair comprising:
   one or more wheelchair brakes;
   means controllable by the operator of the chair for selecting and maintaining an amount of braking force to be applied by said brakes;
   control means responsive to said selecting means for generating a braking signal;
   brake activation means responsive to said signal for proportionately activating said brakes and maintaining the activation of said brakes with the amount of braking force selected by the operator.

2. The system of claim 1 wherein said control means comprises:
   an electrical motor, responsive to said selecting means for rotating by an angular distance selected by the operator in a clockwise or counterclockwise direction;
   means for converting the rotation of said motor to said braking signal.

3. The system of claim 2 wherein said converting means comprises:
   a moveable member; and
   means for converting rotation of said motor to a corresponding substantially linear movement of at least a portion of said member.

4. The system of claim 3 wherein said converting means comprises a cam operatively connected to said motor; and wherein said movable member is a pivotably mounted arm making sliding contact with said cam.

5. The system of claim 4 further comprising means for limiting the amount of possible rotation of said cam.

6. The system of claim 3 wherein said brake is a hydraulic brake and said brake activation means comprises:
   a hydraulic master cylinder including a piston rod operatively connected to said converting means.

7. The system of claim 1 wherein said selecting means comprises:
   first means for transmitting a first selection signal to said control means;
   second means for transmitting a second selection signal to said control means;
   means responsive to operator control for selectively activating said first and said second transmitting means.

8. The system of claim 7 wherein said first transmitting means comprises a pressure switch adapted to be activated by a relatively low pressure;
   and said selection means further comprises a tube connected to said first and said second switches and opening near the mouth of the operator for allowing the operator to apply a relatively high or a relatively low pressure to said first and second switches.

9. The system of claim 7 wherein said operator responsive means comprises:
   means responsive to a first spoken command for activating said first transmitting means; and
   means responsive to a second spoken command for activating said second transmitting means.

10. The system of claim 9 further comprising:
    means responsive to a third spoken command uttered subsequent to said first command and said second command for controlling the duration of the activation of said first and said second transmitting means.

11. The system of claim 1 further comprising:
    means responsive to the activation of said brake for continuing to activate said brake when power to said system is interrupted.

* * * * *